United States Patent [19]

Do et al.

[11] 4,148,216

[45] Apr. 10, 1979

[54] APPARATUS FOR DETERMINING THE VISCOUS BEHAVIOR OF A LIQUID DURING COAGULATION THEREOF

[76] Inventors: Mau T. Do, 28 bis Louis Hubert, 78140 Velizy; Serge H. A. Saffar, 3 Rue Ernest Billiet, 92600 Asnieres; Daniel S. Meimoun, 99 Avenue de Fouilleuse, 92500 Rueil Malmaison, all of France

[21] Appl. No.: 870,529

[22] Filed: Jan. 18, 1978

[51] Int. Cl.² .................. G01N 11/10; G01N 33/16
[52] U.S. Cl. ................................ 73/59; 73/64.1
[58] Field of Search .......................... 73/59, 64.1

[56] References Cited

U.S. PATENT DOCUMENTS

| 3,587,295 | 6/1971 | Simons ............................. 73/64.1 |
| 3,712,117 | 1/1973 | Fitzgerald et al. .................. 73/59 |
| 3,714,815 | 2/1973 | Hartert ............................. 73/64.1 |
| 3,719,075 | 3/1973 | Mandrona et al. .................. 73/64.1 X |

FOREIGN PATENT DOCUMENTS

| 844362 | 7/1952 | Fed. Rep. of Germany ............ 73/59 |
| 1558516 | 1/1969 | France ............................ 73/64.1 |
| 12518 | 4/1972 | Japan ............................... 73/59 |
| 368858 | 4/1973 | U.S.S.R. .......................... 73/64.1 |

*Primary Examiner*—Richard C. Queisser
*Assistant Examiner*—Joseph W. Roskos
*Attorney, Agent, or Firm*—Larson, Taylor & Hinds

[57] ABSTRACT

A thromboelastographic apparatus comprises a body suspended to a resilient tape and immersed in operation in a liquid to be studied. The liquid is received in a receptacle which is oscillated about the axis of the tape with a predetermined frequency and amplitude. The amount of oscillatory movement impressed to the body is measured by induction.

11 Claims, 7 Drawing Figures

APPARATUS FOR DETERMINING THE VISCOUS BEHAVIOR OF A LIQUID DURING COAGULATION THEREOF

BACKGROUND AND SUMMARY OF THE INVENTION

The invention relates to apparatus for determining parameters representative of the coagulation and/or the lysis of a coagulable liquid. It relates more particularly to an apparatus commonly named thromboelastography apparatus, for determining such parameters of the blood or derivatives of blood.

A technique for providing measurement of such parameters utilizes a body immersed in the liquid and suspended to a support via vertical torsion means which tends to return said body to a predetermined angular position about the axis of the torsion means. The liquid is received in a receptacle and an oscillatory movement of predetermined frequency and amplitude about the axis of the torsion means is imparted to the receptacle. The amount of oscillatory movement of the body immersed in the liquid is a measure of the viscosity of the liquid. The change of the amount of oscillatory movement with respect to time provides an information about the changes of the properties of the liquid with time, for instance due to coagulation and/or lysis.

A prior art thromboelastography apparatus utilizes a mirror fixed to a torsion wire for providing an indication on the amount of oscillatory movement of the body. A fixed light source directs a light beam onto the mirror and the beam reflected by the mirror is observed directly on a ground glass screen or photographed on a light-sensitive paper carried by a support which moves transversely to the direction of movement of the beam.

FIG. 1 shows the general shape of the curve envelope of the oscillations recorded on a photographic paper in the case of coagulation and subsequent lysis of a blood sample. The curve of FIG. 1 represents the amplitude x of the oscillatory movement of the beam on the paper plotted against time t. Curve 1 is currently called a "thromboelastogram".

The first part 2 of curve 1 corresponds to the initial phase of the coagulation process, before the appearance of fibrin. This initial phase is revealed on the graph by negligible amplitudes and corresponds to a straight portion, commonly called r. When fibrin appears in the blood sample, the amplitude of the oscillations increases with time to a maximum value after which lysis phenomena occur and the amplitude of the oscillations decreases.

The useful parameters for the analysis of coagulation include, besides the time duration represented by segment r: the maximum amplitude $A_m$ of the oscillations and the time period represented by segment k. The beginning of segment k corresponds to the end of segment r, i.e. to an amplitude of oscillation which does not exceed a predetermined value (for instance 1 mm) on the recording paper under predetermined conditions; its end corresponds to an oscillation amplitude which is for instance 20 mm on the recording paper under the same conditions as above.

When the thromboelastogram is obtained by photographic recording, the different parameters of the coagulation, particularly parameters r, k and $A_m$ are measured manually on the photographic picture. In most cases, development of the photographic picture requires time and appropriate facility. Manual measurements are not accurate. Due to the lack of accuracy, a limited number of parameters representative of the variations of the coagulation and/or the lysis can be measured.

It is an object of the invention to remove the above-mentioned disadvantages and to provide a device which allows accurate measuring of parameters representative of the coagulation and/or of the lysis of a coagulable liquid, typically blood.

It is another object of the invention to provide a direct display of parameters representative of the coagulation and/or lysis.

It is a further object of the invention to provide such a device which is rugged, simple and of low cost.

According to an aspect of the invention, there is provided apparatus for determining the viscous behaviour of a liquid during coagulation and lysis thereof or the like. The apparatus comprises vertical torsion means having an end connected to stationary support means and an oscillatory body suspended to the other end of the vertical torsion means (typically a resilient tape) whereby said torsion means tend to return said body to a predetermined angular position about the axis of the torsion means. The apparatus comprises means for supporting a receptacle for the liquid and for imparting to the receptacle and oscillatory movement of predetermined frequency and amplitude about an axis which is substantially coaxial with the axis of the torsion means. The amount of oscillation of the body, which in operation is immersed in the liquid, is measured by an electric system which makes use of electromagnetic detection. For that purpose, the measuring means comprises electrical induction means having a movable element operatively connected to said body for oscillatory movement therewith and a stationary element having output terminal means of a type which delivers, on said terminal means, an electrical signal whose amplitude is representative of the amplitude of the oscillatory movements of said body, and means for measuring the amplitude of said electrical signal.

The variations of the electric output signal may be displayed, for example by means of a graphic recorder. This signal can also be fed to a computer for determining the above-mentioned parameters, particularly r, k and $A_m$.

In an embodiment of the invention, the inductive movable element is an elongated magnetizable element, e.g. a ferrite bar; this magnetizable element is fast with the torsion means so as to be movable in a plane perpendicular to the axis of the torsion means; in this case, the stationary element may comprise two fixed coils disposed on each side of the movable element so that movement thereof generates a differential induction signal.

The apparatus advantageously comprises demodulator means for generating a signal representing the envelope of the output signal of the induction type sensing means. In this case, the apparatus preferably comprises a comparator for comparing the output signal of the demodulator means with a reference signal representing an oscillation of predetermined amplitude of the torsion means, a clock and counting means for counting the pulses supplied by the generating means. The content of the counting means is stored when the output signal of the demodulator exceeds the reference signal.

SHORT DESCRIPTION OF THE DRAWINGS

FIG. 1, already referred to, shows a thromboelastogram, i.e. a curve of amplitude of movement versus time;

FIG. 4b illustrates a modification of the embodiment of FIG. 4a;

DESCRIPTION OF PREFERRED EMBODIMENTS

Figure 2:
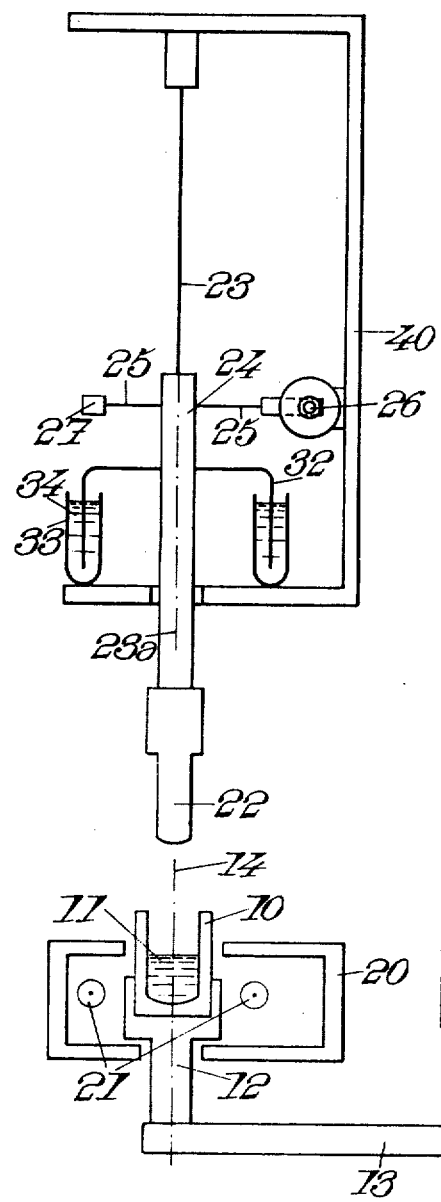
FIG. 2 shows a fraction of a device constituting a first embodiment of the invention.
Figure 6:
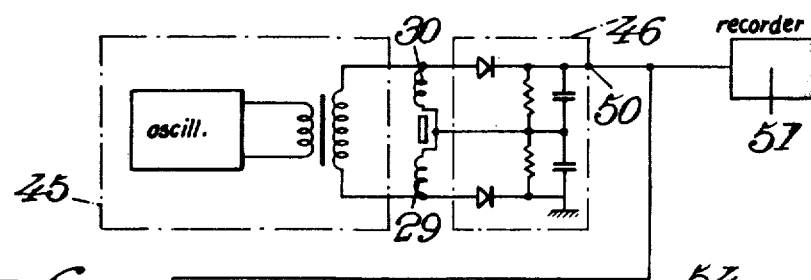
FIG. 6 shows sensing means and computing means for use in the device of the invention.
Figure 6:
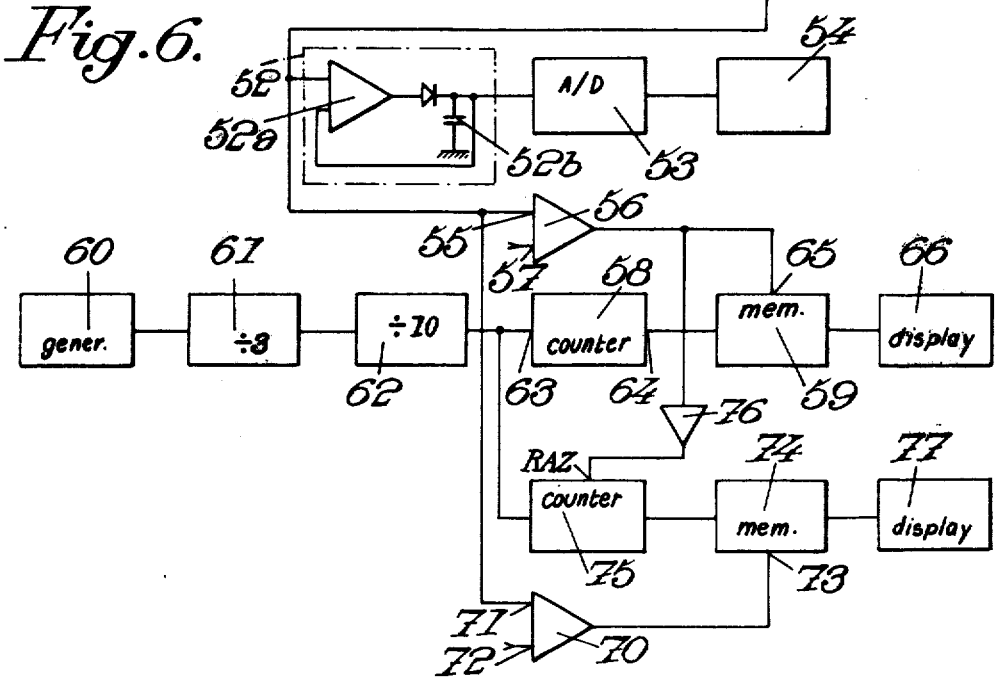

Referring to FIG. 2, there is shown an overall view of a thromboelastrography device. However, the circuitry which processes the electrical signal appearing at the terminals of the sensing means is not shown in FIG. 2, but is shown in FIG. 6.

Referring again to FIG. 2, there is provided a receptacle 10 for containing the coagulable liquid 11 to be studied. Receptacle 10 is disposed on a support 12 fast with a horizontal arm 13 adapted to pivot about an axis 14 which coincides with the axis of support 12 and that of receptacle 10.

Figure 5:
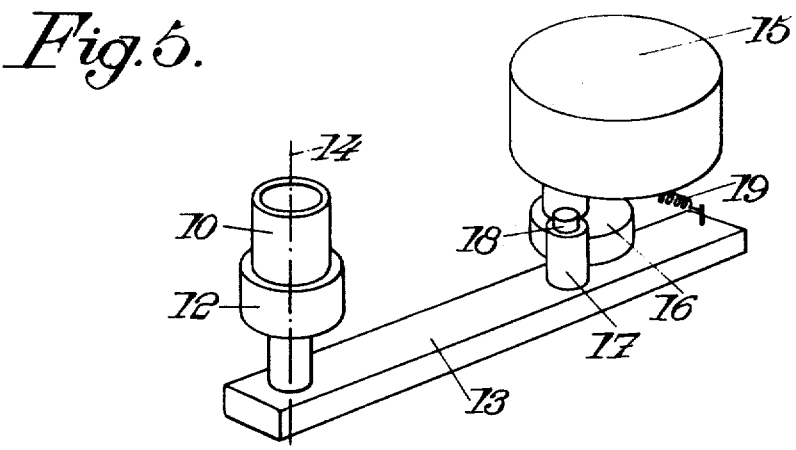
FIG. 5 is an isometric view of means for oscillating the receptacle containing a coagulable liquid suitable for use in the device shown in FIG. 2.

Arm 13 is associated with a motor 15 adapted to oscillate support 12 and receptacle 10 with predetermined amplitude value and frequency about axis 14. For that purpose, motor 15 rotates a horizontal disk 16 about an axis excentric with respect to the disk (FIG. 5). A tubular part 17 is fitted over a vertical pin 18 fast with arm 13. Tubular part 17 is retained in abutment against the periphery of disk 16 by resilient return means such as a spring 19 acting on the end of arm 13 which is remote from axis 14. Finally, in so far as FIG. 5 is concerned, it is important to note that tubular part 17 has a sliding fit on pin 18 so as to limit the wear of part 17.

Receptacle 10 and the upper part of support 12 are located in an enclosure 20 which also accomodate heating resistors 21 for heating the liquid 11 and, in combination with regulating means (not shown), for maintaining the temperature of liquid 11 at a predetermined value, typically 37° C.

The upper portion of the device shown in FIG. 2 comprises a driven cylinder or body 22, which in operation is immersed in liquid 11; in FIG. 2 however, the device has been shown at rest with cylinder 22 being out of receptacle 10. Cylinder 22 is connected to the lower end of a vertical torsion ribbon 23 by an elongated support 24.

The upper part of support 24 carries a horizontal rod 25 extending on each side of the cylinder shaped support 24. An elongated ferrite bar 26 is fixed to a first end of this rod 25. The bar 26 is horizontal and perpendicular to the axis of rod 25. A counter-weight 27 is fitted at the other end of rod 25 so that the centre of gravity of the assembly suspended from the torsion ribbon or tape 23 passes through the axis of said ribbon. Ferrite bar 26 oscillates as indicated by arrows 28 in FIG. 3 when ribbon 23 torsionally oscillates about its axis and is associated with two stationary coils 29 and 30 disposed on each side of said bar 26. The axis of these coils corresponds substantially to the longitudinal direction of bar 26.

Figure 3:
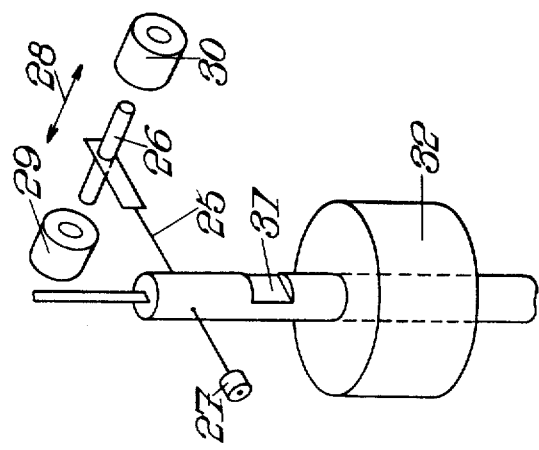
FIG. 3 is an isometric view illustrating the sensing means of the device shown in FIG. 2.

Referring to FIG. 3, the elongated support 24 is formed with a notch 31 located below rod 25. The support may be clamped with a clip (not shown) engaging the notch when cylinder 22 is raised up, i.e. when it is outside receptacle 10; such clamping may facilitate the operation of replacing cylinder 22.

A bell-shaped member 32 is fixed to support 24 below notch 31. Member 32 has a cylindrical wall coaxial with support 24 and which dips into a crown-shaped receptacle 33 having an axis 23a. Receptacle 33 is filled with a liquid 34 such as oil. The assembly formed by bell member 32, receptacle 33 and liquid 34 dampens lateral oscillations of ribbon 23 and of the elements which are suspended from ribbon 23.

Figure 4B:
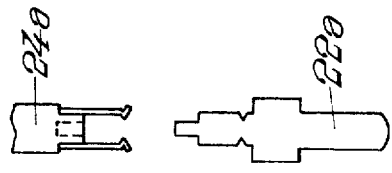
Figure 4A:
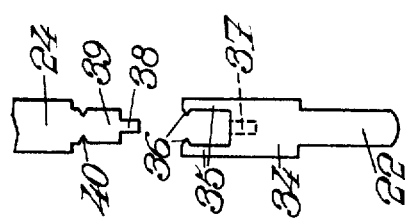
FIG. 4a shows the driven body of the device of FIG. 2 and its support.

In the embodiment of FIG. 4a, driven body 22 is removably fixed to the lower part of support 24. For this purpose, the upper part of cylinder 22 has a cylindrical extension 34a of larger diameter. Extension 34a has resilient lugs 35 each having a projection 36 turned towards the axis of cylinders 22 and 34. A blind aperture 37 is formed in the end surface of cylindrical part 34a. The lower end of support 24 comprises a part 39 to be introduced between blades 35 and a centring pin 38 for location in aperture 37; above part 39, there are provided notches 40 which cooperate with projections 36 so as to lock cylinder 22 in the axial direction.

Cylinder 22 with its extension 34 and blades 35 can be made from metal or preferably from plastics material. In the latter case, cylinder 22 is of low price and can be discarded after use, so as to avoid washing it. Receptacle 10 may be made from the same materials. If a plastics material is used, the advantages are the same as for cylinder 22.

FIG. 4b illustrates a modified embodiment of the cylinder forming the driven body and of the lower part of support 24. In FIG. 4b, the upper part of cylinder 22a is of the male type, whereas the lower part of support 24a is of the female type.

In another modification (not shown), the lower end of support 24 is removable; in this way ends of different shapes may be used, these shapes being chosen so as to permit the use of bodies of different types.

Referring again to FIGS. 2 to 5, the assembly formed by ribbon 23 and the elements secured therewith, as well as coils 29 and 30, are carried by a frame or supporting structure 40 vertically displacable for lifting cylinder 22 clear from receptacle 10 or for introducing it therein.

In operation, an oscillation is imparted to arm 13 and so to receptacle 10; if the liquid has a low viscosity, i.e. if it has not begun to coagulate, the friction forces between tank 10 and liquid 11 as well as between the liquid and cylinder 22 are practically negligible. Ribbon 23 remains motionless (part 2 of curve 1 of FIG. 1). On the other hand, as soon as the liquid begins to coagulate (beginning of segment k), the friction forces of cylinder 22 against the "fibres" in liquid 11 ensure a partial communication of the movements imparted by tank 10 to liquid 11 to cylinder 22; thus ribbon 23 is subjected to torsional oscillations. The amplitude of the oscillations depends on the condition and the degree of coagulation of liquid 11. The differential electrical signal appearing at the terminals of coils 29 and 30 provides an indication of the amplitude of the oscillations of ribbon 23 and is measured as will now be described with reference to FIG. 6. The means for sensing the oscillations of the torsion member are particularly sensitive and that makes it possible to use a torsion ribbon 23 instead of a fragile torsion wire.

Coils 29 and 30 are disposed in electrical series relation. The terminals of said coils are connected to the outputs of an oscillator 45 which applies a high frequency signal (20 kHz for instance) to the terminals of coils 29 and 30. The opposite terminals of the coils and their common terminals are connected to respective inputs of a diode type demodulator unit 46.

The differential signal caused by movement of the ferrite bar 26 between coils 29 and 30 modulates the amplitude of the high frequency signal. Unit 46 demodulates the signal applied to its terminals and supplies at its output 50 a signal representing the envelope of the variations of the differential signal. Due to the use of high frequency, coils 29 and 30 may have small dimensions.

The output 50 of unit 46 is connected to the input of a graphic recorder 51. The travel speed of the paper and the sensitivity are selected for consistency with the usual scales of thrombelastographs. An advantageous feature of such a recorder 51 is that a thrombelastogram is obtained without delay and its trend can be observed during the coagulation and/or lysis process without having to wait, as with some previous devices, for the development of a photographic paper. Moreover, it is possible to use any type of recorder provided that this latter allows the usual scales of thrombelastograms to be obtained. Furthermore, there is no need for a special support for the moving paper.

Output 50 of unit 46 is also connected to the input of a device 52 of the peak detecting and storing type. As illustrated, device 52 comprises an operational amplifier 52a and a storage capacitor 52b. Device 52 supplies at its output an analog signal which is applied to the input of an analog/digital converter 53 connected to the input of a display unit 54. The digital value observed at unit 54 corresponds to quantity $A_m$ (FIG. 1).

The first input 55 of a comparator 56 is connected to the output 50 of unit 46. The second input 57 of comparator 56 is connected to a reference source (not shown) adapted to deliver a low value signal which represents a low amplitude oscillation of ribbon 23. Referring to the diagram of FIG. 1, the value of the signal applied to input 57 of comparator 56 corresponds to a width $x = 1$ mm.

Figure 1:
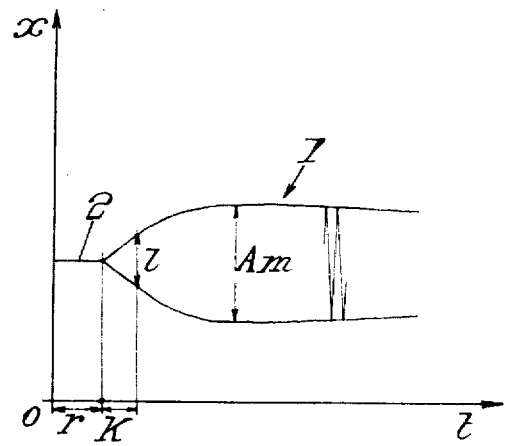

Comparator 56 is associated with a counter 58, a time base or clock and a latching memory 59 for determining the end of segment r (FIG. 1). The clock comprises a generator 60 of periodic pulses of predetermined frequency, 1 Hz for instance. In the embodiment of FIG. 6, the output of generator 60 is connected to the input of a first divider 61 whose factor of division is 3. The output of divider 61 feeds the input of a second divider 62 whose factor of division is 10. Therefore, divider 62 provides at its output a pulse every 30 seconds. These pulses are applied to the counting input 63 of counter 58. The latter has an output 64 connected to the input of latching memory 59. The latter comprises a stop input 65 connected to the output of comparator 56. Finally, the output of said memory is connected to the input of a digital display unit 66.

In operation, the content of counter 58 is transferred to memory 59. The information applied to the input of this memory is without effect after a signal has been applied to its stop input 65. This stop signal appears as soon as the amplitude of the oscillation of ribbon 23 exceeds a predetermined value corresponding to $x = 1$ mm on the thrombelastogram. The digital value displayed by member 66 corresponds then to segment r.

A second comparator 70 comprises a first input 71 connected to the output 50 of unit 46. The second input 72 of comparator 70 is connected to a reference source providing a signal of predetermined value. This value represents a width l equal to 20 mm on the diagram of FIG. 1. The output of comparator 70 is connected to the stop input 73 of a second latching memory 74 whose input is connected to the output of divider 62. The "clear" input RAZ of counter 75 is connected to the output of comparator 56 through an inverter 76. Finally, the output of counter 74 is connected to the input of a digital display unit 77.

In operation, counter 75 counts the pulses appearing at the output of divider 62 as soon as the amplitude of the oscillations of ribbon 23 exceeds a value corresponding to $x = 1$ mm on the diagram of FIG. 1. The content of this counter is transferred to memory 74. This transfer is interrupted when a signal appears at the output of comparator 70, i.e. when the oscillation amplitude of ribbon 23 reaches a value corresponding to $l = 20$ mm (FIG. 1). The numerical value displayed by unit 77 corresponds then to the time (or segment) k of FIG. 1.

In a particular embodiment, generator 60 is a MOTOROLA MM 3516. The output of this circuit is connected directly to a display unit (not shown) allowing the time to be read in hours, minutes and seconds. Said circuit comprises a stop input which can be used for displaying a time corresponding to a particular phenomenon, e.g. amplitude $A_m$. To this end, the output of comparator 56 can be connected to said stop input.

The apparatus which has just been described with reference to the figures can lend itself to numerous variations without departing from the spirit of the invention.

In particular, the digital data relative to quantities $A_m$, r and k may be recorded on a printer which replaces, or complements, display units 54, 66 and 77.

Moreover, referring to the arrangements shown in FIG. 6, computing means are provided which determine the magnitudes of certain parameters. With means similar to those shown in FIG. 6, particularly comparator means, counting means and a clock, it is possible to determine the values of other parameters directly. Thus for example after determination of magnitude $A_m$ it is possible to study fibrinolysis as well as hyper- and hypo-coagulability or more generally any parameter derived from r at the end of the lysis.

By way of example, computing means (not shown) can be associated with memories 59 and 74 to determine the so-called PT index of thrombodynamic potential. This index is defined by the relationship:

$$PT = Emx/K$$

with $$Emx = 100Am/(100 - Am)$$

An important use of the apparatus is in the field of biology and more particularly of hemiobiology. It permits in particular the study of coagulolytic phenomena of whole blood or of certain of its fractions (platelet rich plasma, plasma without platelets, serum, etc.). It also permits the study of the effect of pharmalogical drugs liable to affect the coagulolytic characteristics of the blood or its fractions. Finally, the addition of a chemical or enzymatic reagent can permit the analytic study of the different steps of the coagulation or lysis process, particularly owing to the clock and the storage of the displayed times; for example, the thrombine time, Howell's time, Quick's time, coagulation time, cephalin time and Kaolin cephalin time can be determined. That list is not limitative.

It will be appreciated that the device of the invention enables determination and display of the parameters studied by previously known thrombelastography devices with increased accuracy and achieves analytical examinations relative to the coagulolytic phenomena, which cannot be made with the previously known devices. The device of the invention can be considered as being a multi-purpose apparatus permitting comprehensive measurements to be carried out rather than just another type of thrombelastography device.

We claim:

1. Apparatus for determining the viscous behaviour of a liquid during coagulation and lysis thereof and the like, comprising:
    support means,
    vertical torsion means having an end connected to said support means,
    an oscillatory body suspended to the other end of said vertical torsion means, whereby said torsion means tends to return said body to a predetermined angular position about the axis of the torsion means,
    means for supporting a receptacle for said liquid and for imparting to said receptacle an oscillatory movement of predetermined frequency and amplitude substnatially about said axis,
    and amplitude measuring means for measuring the amplitude of the oscillations of said oscillatory body when immersed in said liquid,
    said amplitude measuring means comprising:
    electrical induction means having a movable element operatively connected to said body for oscillatory movement therewith and a stationary element, having output terminal means, for delivering to said terminal means, an electrical signal whose amplitude is representative of the amplitude of the oscillatory movements of said body,
    and means for measuring the amplitude of said electrical signal.

2. Apparatus according to claim 1, wherein said movable element comprises an elongated magnetic element carried by said torsion means and arranged for movement transversely to the axis of said torsion means and wherein the stationary means include two stationary coils located on either side of said magnetic element whereby the movement of said magnetic element induces a signal in said coils.

3. Apparatus according to claim 2, wherein the magnetic element is a ferrite bar.

4. Apparatus according to claim 1, further comprising demodulating means connected to said output terminal means, for delivering a signal representative of the envelope of the electrical signals on said terminal means.

5. Apparatus according to claim 4, further comprising recording means for displaying the variations of the output signal of the demodulating means with time.

6. Apparatus according to claim 4, further comprising comparator means having a first input connected to receive the output signal of the demodulating means and a second input connected to receive a reference signal, clock means for delivering pulses at a predetermined frequency of an output terminal thereof, counting means having an input terminal connected to receive the pulses from said clock means, memory means for storing the content of the counting means, said memory means having a stop input connected to the output of the comparating means whereby the content of the counting means is stored at the time where the output signal of the demodulating means exceeds the reference signal, and means for displaying the contents of said memory means.

7. Apparatus according to claim 6, wherein said reference means represents an oscillatory movement of low amplitude as compared with the amplitude of the oscillatory movement of the said body, said apparatus further comprising second comparator means for comparing the output signal of said demodulating means and a second reference means representing a predetermined value of the amplitude of the oscillatory movement of said body, second counting means for counting the pulses delivered by the clock means, means for triggering counter by said second counting means upon said output signal of the demodulating means exceeding said first reference signal, second memory means for storing the content of said counting means and having a stop input connected to the output of the second comparator means whereby the content of said second counting means is stored when the value of the output signal of the demodulating means exceeds the value of said second reference means, and means for displaying the content of said second memory means.

8. Apparatus according to claim 4, further comprising peak detection and storing means connected to receive the output signal of the demodulating means.

9. Apparatus according to claim 1, wherein the vertical torsion means is a tape of resilient material.

10. Apparatus according to claim 9, further comprising a cylindrical elongated body permanently connected to said second end of said torsion means and removably connected to said body.

11. Apparatus according to claim 10, further comprising means for dampening radial oscillations of said cylindrical support means, said dampening means having a cylindrical wall secured to said cylindrical support means coaxially thereto and an annular cup for receiving a liquid in a position such that said cylindrical wall dips into said liquid.

* * * * *